United States Patent [19]

Masuhara et al.

[11] Patent Number: 5,147,202
[45] Date of Patent: Sep. 15, 1992

[54] BRACKET FOR ORTHODONTICS

[75] Inventors: Eiichi Masuhara, Tokyo; Shigeo Komiya, Urawa; Kiyomi Sanbonmatsu, Yomo, all of Japan

[73] Assignee: Japan Institute of Advanced Dentistry, Tokyo, Japan

[21] Appl. No.: 260,639

[22] Filed: Oct. 21, 1988

[30] Foreign Application Priority Data

Oct. 22, 1987 [JP] Japan ................... 62-265434
Jul. 6, 1988 [JP] Japan ................... 63-166775
Jul. 6, 1988 [JP] Japan ................... 63-166776

[51] Int. Cl.$^5$ ............................................. A61C 3/00
[52] U.S. Cl. ......................................... 433/8; 433/9; 433/10
[58] Field of Search ................................ 433/8, 9, 10

[56] References Cited

U.S. PATENT DOCUMENTS 4,948,366 8/1990 Horn et al. ............................. 433/8
5,071,344 12/1991 Wong et al. ............................ 433/8

Primary Examiner—V. Millin
Attorney, Agent, or Firm—Armstrong, Nikaido, Marmelstein, Kubovcik & Murray

[57] ABSTRACT

A bracket for orthodontics having a bracket body made of a composite resin material and a thin layer of a synthetic resin material in a dental adhesive. The synthetic resin layer is laminated on the base surface of the bracket body in such a manner that the composite resin material of the bracket body and the synthetic resin of the thin layer are mingled with each other at the boundary therebetween. The thin resin layer is composed of polymethyl methacrylate having an average molecular weight of 1,000,000 or less or a polymethacrylate copolymer.

3 Claims, 3 Drawing Sheets

BRACKET FOR ORTHODONTICS

BACKGROUND OF THE INVENTION

The present invention relates to a bracket for orthodontics and, more particularly, to an orthodontic bracket having excellent aesthetic properties and enhanced strength as well as strong adhesion to the tooth.

In orthodontic devices for correcting irregularities of teeth, a bracket is used as a means for connecting together a wire and a band.

In actual use, the bracket is rigidly secured to the surface of a tooth which is desired to be straightened in order to apply thereto a flexural or tensile load derived from the wire. For this purpose, metallic brackets have heretofore been generally used, and recently plastic and ceramic brackets have also been put into practical use.

Metallic brackets have the advantage that they have superior strength and enable straightening force from a wire or the like to be effectively transmitted to the teeth, but they are inferior in terms of aesthetic properties. On the other hand, ceramic brackets have excellent transparency and therefore are superior from the aesthetic viewpoint, but they are generally considered to be relatively brittle and inferior in terms of adhesive properties.

Conventional plastic brackets have superior aesthetic and adhesive properties and therefore widely used for the edgewise method and the like but they are inferior in terms of strength.

Conventional plastic brackets suffer from the following clinical problems: (1) the wing portions thereof are readily fractured; (2) these brackets are apt to discolor; (3) the wire is unable to slide smoothly; (4) it is impossible to provide siamese type brackets which can be used for 21 | 12; and (5) it is impossible to provide torque angulation.

Plastic brackets which are now widely used are made of thermoplastic polycarbonates. Polycarbonates, which have good transparency and excellent impact resistance, are generally used as engineering plastics. However, brackets made of thermoplastic polycarbonates are insufficient for use in orthodontics because of relatively low surface hardness and somewhat low mechanical strength (i.e., tensile strength, flexural strength and compressive strength), and therefore the polycarbonate brackets do not necessarily exhibit satisfactory functions as orthodontic devices. Since the surfaces of the plastic brackets are not satisfactorily hard the bracket surfaces are likely to be scratched with toothbrushes or the like, which leads to wear and contamination (discoloration). In addition, since the mechanical strength of the conventional plastic brackets is inadequate, the wing portions thereof are readily fractured as described above. Therefore, it is difficult to use such conventional plastic materials to produce brackets having various configurations (i.e., siamese type brackets, brackets provided with torque angulation, etc.) which are needed for orthodontics.

It should be noted that typical examples of adhesives for orthodontic brackets which may be used to carry out orthodontics include 4-methacryloyloxyethyltrimellitic acid anhydride, methyl methacrylate monomers, mixed compositions of polymethyl methacrylate powders and tributylborane (TBB) [e.g., "Superbond C&B" (trade name) manufactured by Sun Medical Co., Ltd.), and mixed compositions of methyl methacrylate monomers, BisGMA, BPO and a tertiary amine (redox system type).

SUMMARY OF THE INVENTION

The present inventors made exhaustive studies in order to solve the above-described problems and, as a result, have developed a material which may be most suitably used as a material for brackets for orthodontics by making some improvements on an acrylic composite resin material which has heretofore been used as a restrorative material The present invention has been accomplished on the basis of the development of said material.

More specifically, according to a first technical idea of the present invention, there is provided a bracket for orthodontics formed from a bracket material obtained by polymerizing and setting a mixture consisting essentially of:

(a) from 40 to 90% by weight of a multifunctional methacrylate and/or a multifunctional acrylate;

(b) from 9 to 50% by weight of a monofunctional methacrylate and/or a monofunctional acrylate;

(c) from 1 to 30% by weight of a filler; and (d) from 0.01 to 2.0% by weight of a polymerization initiator.

According to a second technical idea of the present invention, the followings are provided:

(1) A bracket for orthodontics comprising a bracket body made of a composite resin material and a thin layer of a synthetic resin material which is partly soluble or swellable in a dental adhesive, the synthetic resin thin layer being laminated on the base surface of the bracket body in such a manner that the composite resin material constituting the bracket body and the synthetic resin material constituting the thin layer are mingled with each other at the boundary therebetween.

(2) A bracket for orthodontics as defined in (1), wherein the composite resin material that constitutes the bracket body is formed by polymerizing and setting a mixture consisting essentially of (a) from 40 to 80% by weight of a multifunctional methacrylate and/or a multifunctional acrylate, (b) from 9 to 50% by weight of a monofunctional methacrylate and/or a monofunctional acrylate, (c) from 5 to 80% by weight of a filler, and (d) from 0.01 to 2% by weight of a polymerization initiator, and the synthetic resin thin layer laminated on the base surface of the bracket body is formed by polymerizing and setting a mixture consisting essentially of (e) from 30 to 70% by weight of a monofunctional methacrylate, (f) from 30 to 70% by weight of either a polymethacrylate or a copolymer thereof, and (g) from 0.01 to 1% by weight of a polymerization initiator.

(3) A process for producing an orthodontic bracket comprising the steps of: supplying a composite resin paste into a mold; placing on the bracket base forming surface of the composite resin paste a thin layer of a synthetic resin paste which is partly soluble or swellable in a dental adhesive; and polymerizing and then setting these materials.

According to a third technical idea of the present invention, the followings are provided:

(1) A bracket for orthodontics comprising a bracket body made of a composite resin material A obtained by polymerizing and setting a mixture consisting essentially of
  (a) from 40 to 80% by weight of a multifunctional methacrylate and/or a multifunctional acrylate,
  (b) from 9 to 50% by weight of a monofunctional methacrylate and/or a monofunctional acrylate,
  (c) from 5 to 80% by weight of a filler, and
  (d) from 0.01 to 2% by weight of a polymerization initiator,
  and a thin layer of a composite resin material B obtained by polymerizing and setting a mixture consisting essentially of
  (e) from 5 to 24% by weight of a multifunctional methacrylate,
  (f) from 0 to 24% by weight of a monofunctional methacrylate,
  (g) from 50 to 90% by weight of a silica filler, and
  (h) from 0.01 to 1% by weight of a polymerization initiator,
  the thin layer of the composite resin material B being laminated on the base surface of the bracket body in such a manner that the composite resin material A constituting the bracket body and the composite resin material B constituting the thin layer are mingled with each other at the boundary therebetween.

(2) A process for producing an orthodontic bracket comprising the steps of:
  supplying into a mold a composite resin paste A consisting essentially of
  (a) from 40 to 80% by weight of a multifunctional methacrylate and/or a multifunctional acrylate,
  (b) from 9 to 50% by weight of a monofunctional methacrylate and/or a monofunctional acrylate,
  (c) from 5 to 80% by weight of a filler, and
  (d) from 0.01 to 2% by weight of a polymerization initiator;
  placing on the base forming surface of the composite resin paste A a composite resin paste B consisting essentially of
  (e) from 5 to 24% by weight of a multifunctional methacrylate,
  (f) from 0 to 24% by weight of a monofunctional methacrylate,
  (g) from 50 to 90% by weight of a silica filler, and
  (h) from 0.01 to 1% by weight of a polymerization initiator; and
  polymerizing and setting these materials.

Since the above-described orthodontic brackets according to the present invention have considerably high fracture strength compared with the conventional plastic (polycarbonate) brackets, it is possible to produce siamese type brackets for the front teeth and brackets with torque angulation, which have heretofore been impossible to produce because of the inadequate mechanical strength of the plastic materials for the prior art.

Since the orthodontic brackets according to the present invention are excellent in terms of various mechanical properties, i.e., tensile strength, flexural strength, compressive strength, etc., it is also possible to reduce the required size of the brackets. Therefore, a patient who has such a bracket attached to his tooth feels less uncomfortable with the foreign matter in his mouth.

The brackets according to the present invention, which are semi transparent, have excellent aesthetic properties, and since the hardness thereof is sufficiently high, the straightening wire is able to slide smoothly and there is no fear of the surface of the bracket being contaminated due to scratches which would otherwise be made with a toothbrush or the like.

Accordingly, the brackets of the present invention not only have satisfactory initial strength but also exhibit high mechanical strength over a long period of time and therefore are free from the fear of fracture or surface contamination even if they are used for a long time.

In addition, the provision of the above-described specific thin layer on the base surface of the bracket body enables satisfactory improvement in the adhesion of the bracket to the tooth.

DESCRIPTION OF THE PREFERRED EMBODIMENTS

The present invention has been accomplished on the basis of the development of a material suitable for orthodontic brackets.

First Technical Idea of the Invention

According to the first technical idea of the present invention, there is provided an orthodontic bracket which has superior aesthetic properties and enhanced mechanical strength.

More specifically, the present invention provides a bracket for orthodontics which is formed from a bracket material obtained by polymerizing and setting a mixture consisting essentially of:
  (a) from 40 to 90% by weight of a multifunctional methacrylate and/or a multifunctional acrylate;
  (b) from 9 to 50% by weight of a monofunctional methacrylate and/or a monofunctional acrylate;
  (c) from 1 to 30% by weight of a filler; and
  (d) from 0.01 to 2.0% by weight of a polymerization initiator.

Examples of multifunctional methacrylates usable in the present invention include dimethacrylates such as ethylene glycol dimethacrylate, diethylene glycol dimethacrylate, triethylene glycol dimethacrylate, tetraethylene glycol dimethacrylate, 1,4-butanediol dimethacrylate, 1,3-butanediol dimethacrylate, 2,2-bis-[4-(2-hydroxy-3-methacryloxypropoxy)phenyl] propane, 2,2-bis-(4-methacryloxyphenyl) propane, 2,2-bis-(4-methacryloxyethoxyphenyl) propane, 2,2-bis-(4-methacryloxypolyethoxyphenyl) propane, and di(methacryloxyethyl) trimethylhexamethylenediurethane, trimethacrylates such as trimethylolpropane trimethacrylate, and tetramethylolmethane trimethacrylate, tetramethacrylates such as tetramethylolmethane tetramethacrylate, and hexamethacrylates such as dipentaerythritol hexamethacrylate.

Examples of multifunctional acrylates usable in the present invention include diacrylates such as ethylene glycol diacrylate, diethylene glycol diacrylate, triethylene diacrylate, tetraethylene glycol diacrylate, 1,4-glycol butanediol diacrylate, 1,3-butanediol diacrylate, 2,2-bis-[-4-(2-hydroxy-3-acryloxypropoxy)phenyl] propane, 2,2-bis-(4-acryloxyphenyl) propane, 2,2-bis-(4-acryloxyethoxyphenyl) propane, 2,2-bis-(4-acryloxypolyethoxyphenyl) propane, and di-(acryloxyethyl) trimethylhexamethylenediurethane, triacrylates such as trimethylolpropane triacrylate and tetramethylolmethane triacrylate, tetraacrylates such as tetramethylolmethane tetraacrylate, and hexaacrylates such as dipentaerythritol hexaacrylate.

Examples of monofunctional methacrylates usable in the present invention include methyl methacrylate, ethyl methacrylate, isopropyl methacrylate, n-butyl methacrylate, 2-ethylhexyl methacrylate, cyclohexyl methacrylate, phenyl methacrylate, benzyl methacrylate, and isobornyl methacrylate.

Examples of monofunctional acrylates usable in the present invention include methyl acrylate, ethyl acrylate, isopropyl acrylate, n-butyl acrylate, 2-ethylhexyl acrylate, cyclohexyl acrylate, phenyl acrylate, benzyl acrylate, isobornyl acrylate, trimethylsilylpropyl acrylate, tris-trimethylsiloxanylsilyl acrylate and trifluoromethyl acrylate.

Examples of fillers usable in the present invention are inorganic and organic fillers.

Examples of inorganic fillers include finely-crushed glass, finely-ground quartz, alumina fine powder and other ceramic fine powders. A silica filler surface-treated with a silane coupling agent is one of the preferable inorganic fillers.

Preferable examples of organic fillers are finely divided particles obtained by grinding a dimethacrylate, trimethacrylate, tetramethacrylate, hexamethacrylate, diacrylate, triacrylate, tetraacrylate, hexaacrylate or the like after polymerization, or finely divided particles obtained by pearl polymerization of these materials.

As to the polymerization initiator, (1) in the case of heat polymerization, those which are generally used, for example, organic peroxides and azobis compounds, may be employed; (2) in the case of cold polymerization, for example, a combination of a peroxide and a tertiary amine may be employed.

Further, (3) in the case of photopolymerization, it is possible to employ a combination of a peroxide and a photosensitizer or a combination of a photosensitizer and a reducing agent.

Examples of photosensitizers usable in the present invention include those which are employed for ultraviolet curing, such as benzophenones. Particularly preferable examples of photosensitizers are those which are employed for visible light curing, for example, a combination of camphorquinone and a tertiary aimine.

The following is a description of the reasons why the amounts of the components (a) to (d) used in the present invention are restricted within the above described ranges.

(a) If the amount of a multifunctional methacrylate and/or a multifunctional acrylate is out of the range of from 40 to 90% by weight, for example, if it is less than 40% by weight, the fracture strength of the wings of the resulting bracket lowers, which results in an unsatisfactory product, whereas, if said amount exceeds 90% by weight, the wings of the bracket become brittle and the fracture strength thereof also lowers, which results in an unfavorable product.

(b) If the amount of a monofunctional methacrylate and/or a monofunctional acrylate used in the present invention is out of the range of from 9 to 50% by weight, for example, if it is less than 9% by weight, the bracket material becomes brittle and the fracture strength of the wings of the resulting bracket lowers, whereas, if said amount exceeds 50% by weight, the tensile strength of the bracket material lowers and the fracture strength of the wings of the bracket becomes unsatisfactory.

(c) If the amount of a filler used in the present invention is out of the range of from 1 to 30% by weight, for example, if it is less than 1% by weight, the compressive strength of the bracket material lowers, whereas, if said amount exceeds 30% by weight, the tensile strength of the material lowers and the fracture strength of the wings of the resulting bracket lowers to an unsatisfactory level.

(d) If the amount of a polymerization initiator used in the present invention is out of the range of from 0.01 to 2% by weight, for example, if it is less than 0.01% by weight, an unpolymerized substance is left in the reaction product, whereas, if said amount exceeds 2% by weight, the bracket material becomes brittle and the fracture strength of the wings of the resulting bracket lowers, which results in an unfavorable product.

Accordingly, it is preferable to use each component of the present invention within the range specified as described above.

More preferable ranges for the components are as follows: (a) from 50 to 80% by weight of a multifunctional methacrylate and/or a multifunctional acrylate; (b) from 15 to 45% by weight of a monofunctional methacryate and/or a monofunctional acrylate; (c) from 1 to 20% by weight of a filler; and (d) from 0.01 to 2.0% by weight of a polymerization initiator.

The following is a description of a method of producing the orthodontic bracket according to the present invention.

The bracket for orthodontics may be formed by various methods, for example, a method wherein the polymerized plastic material is machined (e.g., cutting, grinding, etc.), or a method wherein a mixture of materials such as a monomer, prepolymer, etc. is polymerized and set in a mold.

Examples of molds usable in the present invention include those which are made of metallic, ceramic, glass or resin materials. In the case of heat or cold polymerization, it is possible to use a mold made of a metallic, ceramic or glass material. In the case where molding process is carried out by photopolymerization, it is possible to use a mold made of a glass, light-transmitting resin or ceramic material.

The synthetic resin material according to the present invention obtained by polymerization and setting is much superior to the conventional polycarbonate material in terms of various mechanical properties.

In particular, the Brinell hardness of the bracket material according to the present invention is about twice that of the polycarbonate material, the compressive strength of the former is about five times that of the latter, and the tensile and flexural strengths of the former are also 30 to 40% higher than those of the latter. The fracture strength (described later in detail) of the bracket according to the present invention is 30 to 50% higher than that of the prior art.

With these excellent mechanical properties, the orthodontic bracket of the present invention is incomparably superior to the prior art.

In the case of a polycarbonate bracket, since the hardness thereof is not sufficiently high, the ligating wire cuts into the bracket surface during the straightening operation, so that the wire is unable to slide smoothly, whereas, in the case of the bracket of the present invention, there is no possibility of the wire cutting into the bracket surface and it is therefore possible to ensure smooth slide of the wire. In addition, since the bracket surface is hard and therefore unlikely to be scratched with a toothbrush, the bracket is free from surface contamination.

Further, the bracket of the present invention is capable of satisfactorily bearing various kinds of stress and load which may be applied thereto in actual use, and therefore there is no fear of the bracket being damaged or fractured even if it is used for a long period of time.

The present invention will be explained more specifically below by way of Examples and Comparative Example. However, the present invention is in no way restricted to these Examples.

EXAMPLE 1-1

Thirty-eight parts by weight of methyl methacrylate, 52 parts by weight of 2,2-bis-(4-methacryloxypolyethoxyphenyl) propane, 10 parts by weight of Aerosil R972 (silika fine powder manufactured by Nihon Aerosil) and 0.3 part by weight of benzoyl peroxide were mixed together and stirred vigorously. Thereafter, the mixture was subjected to vacuum deaeration to remove completely air bubbles from the mixture.

Figure 1:
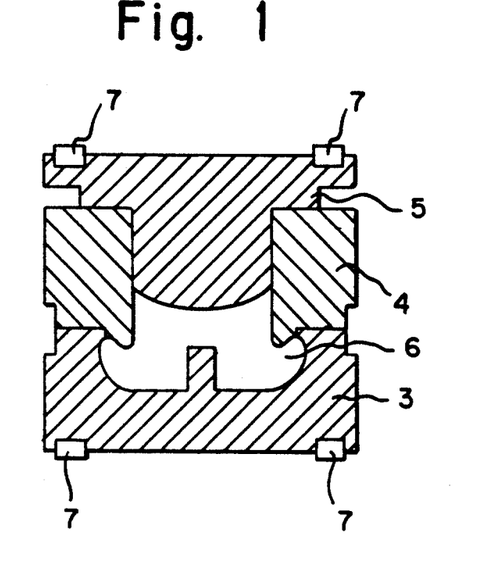
FIG. 1 is a sectional view of a mold used to produce an orthodontic bracket according to one embodiment of the present invention.

The mixture was then poured into a cavity 6 defined inside the lower and side mold members 3 and 4 of a mold made of a stainless steel shown in FIG. 1, and then the upper mold member 5 was forced into the cavity 6. Thereafter, the mold was fixedly clamped from the upper and lower sides thereof by means of leaf springs 7 having a U-shaped cross-section The mold was then maintained in a constant temperature bath at 80° C. for 2 hours to polymerize and set the contents of the mold. Thereafter, the resulting molded bracket was removed from the mold.

It should be noted that the mold shown in FIG. 1 is a split mold which consists of a lower mold member 3, a side mold member 4 and an upper mold member 5, which define in combination a cavity 6 for forming a bracket.

The siamese type bracket thus obtained had excellent properties. More specifically, the fracture strength of the wings thereof was 10.5 kg, and the bracket was semi-transparent and therefore also excellent in terms of aesthetic properties.

Figure 3:
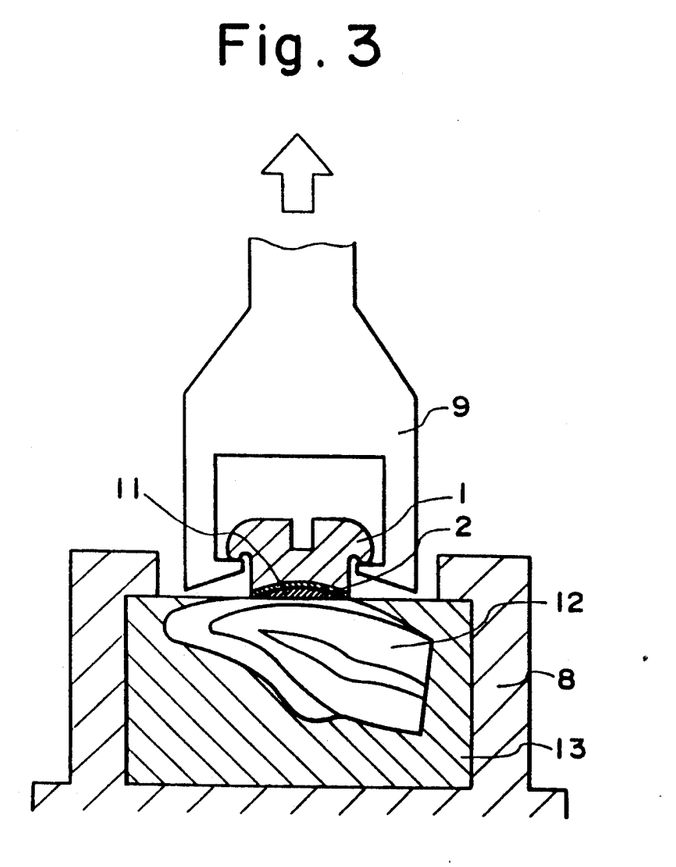
FIG. 3 illustrates a method of measuring the fracture strength of the wing portion of an orthodontic bracket.

The fracture strength of the wings was tested using an Instron universal tester, as shown in FIG. 3. More specifically, the bracket 1 was bonded to the surface of the enamel of a bovine tooth 12 using Superbond 11 (an adhesive manufactured by Sun Medical Co., Ltd.), the proximal portion of the bovine tooth 12 being buried in a resin 13, and this test specimen was attached to a retainer 8 made of steel. Then, the entire wing portion of the bracket 1 was held with a grab-shaped holding member 9 and the holding member 9 was pulled upward. The fracture strength of the wing portion was expressed in terms of the level of load measured at the time when the wing portion was fractured or deformed.

EXAMPLE 1-2

Forty-five parts by weight of cyclohexylmethyl methacrylate, 40 parts by weight of 2,2-bis-(P-2'-hydroxy-3'-methacryloxypropoxyphenyl) propane, 10 parts by weight of 4,8-di-(methacryloxymethylene) tricyclo [5,2,1,0$^{2'6}$] decane, 5 parts by weight of Aerosil R972 (manufactured by Nihon Aerosil), and 0.5 part by weight of lauroyl peroxide were mixed together and vigorously stirred. Thereafter, the procedure of Example 1-1 was repeated to produce a bracket.

The fracture strength of the wing portion of the siamese type bracket thus obtained was found to be 11.1 kg as a result of the testing carried out using the same testing apparatus as in Example 1-1. The bracket was semitransparent and therefore also excellent in terms of aesthetic properties.

EXAMPLE 1-3

Five parts by weight of finely-divided powder of trimethylolpropane trimethyl methacrylate polymer, 40 parts by weight of methyl methacrylate, 10 parts by weight of KAYARAD-DPCA60 (a pentaerythritol hexamethacrylate multifunctional acrylate manufactured by Nippon Kayaku Co., Ltd.), 45 parts by weight of 2,2-bis-(4-methacryloxy diethoxyphenyl) propane, 0.5 part by weight of benzoyl peroxide, and 0.2 part by weight of camphorquinone were mixed together and stirred vigorously. Then, the mixture was subjected to vacuum deaeration to remove completely air bubbles from the mixture.

Then, the mixture was poured into a transparent polypropylene mold of the same type as that shown in FIG. 1, and the mold was fixedly clamped from the upper and lower sides thereof by means of springs having a U-shaped cross-section. Thereafter, the mold was irradiated with light for 15 minutes on the turntable of a visible light irradiator α-Light (manufactured by K.K. Morita Tokyo Seisakusho). The fracture strength of the wing portion of the resulting siamese type bracket was 11.7 kg. The bracket was semi-transparent and therefore also excellent in terms of aesthetic properties.

COMPARATIVE EXAMPLE 1-1

A polycarbonate bracket having the same configuration as that of the bracket obtained in Example 1-1 was produced by injection molding process, and the fracture strength of the wing portion of the resulting bracket was measured in the same way as in Example 1-1.

When tensile load was applied to the wing portion of the polycarbonate siamese type bracket by using the same testing apparatus as in Example 1-1, the wing portion was deformed at a load of 4.2 kg to such an extent that the bracket could not be used for clinical purposes.

Mechanical characteristics of the brackets produced in the above-described Examples and Comparative Example are shown in Table 1-1.

As will be clear from the results shown in Table 1, the bracket material according to the present invention is markedly superior to the polycarbonate bracket material prepared in Comparative Example 1-1 in terms of all the measured properties, i.e., hardness, tensile strength, flexural strength and compressive strength.

TABLE 1-1

|  | Brinell hardness | Tensile strength | Flexural strength | Compressive strength |
|---|---|---|---|---|
| Example 1-1 | 22 | 85 | 121 | 382 |
| Example 1-2 | 26 | 80 | 119 | 368 |
| Example 1-3 | 25 | 81 | 128 | 410 |
| Comp. Ex. 1-1 | 13 | 62 | 92 | 85 |

*The unit of tensile strength, flexural strength and compressive strength is MPa.

As has been described above by way of Examples, the orthodontic bracket according to the present invention has at its wing portion considerably high fracture strength, that is, fracture strength which is several times that of the conventional plastic brackets and the bracket of the present invention, which is semi-transparent, also has excellent aesthetic properties.

Accordingly, it is possible to produce siamese type brackets for 21 | 12 and brackets with torque angulation, which have heretofore been impossible to produce because of the inadequate mechanical strength of the plastic materials for the prior art.

Since the orthodontic bracket according to the present invention is excellent in terms of various mechanical properties, i.e., tensile strength, flexural strength, compressive strength, etc., it is also possible to reduce the required size of the bracket. Therefore, a patient who has this bracket attached to his tooth feels less uncomfortable with the foreign matter in his mouth.

Since the surface hardness of the bracket according to the present invention is markedly higher than that of the prior art, there is no fear of the surface of the bracket being contaminated due to scratches which would otherwise be made with a toothbrush or the like.

Thus, the bracket according to the present invention not only has satisfactory initial strength but also exhibits high mechanical strength over a long period of time and therefore is free from the fear of fracture or surface contamination even if it is used for a long time.

Second Technical Idea of the Invention

According to the second technical idea of the present invention, there is provided a bracket for orthodontics which has superior aesthetic properties and enhanced mechanical strength and further has improved adhesion to the tooth.

Although the above-described orthodontic bracket according to the first technical idea of the present invention is excellent in terms of various mechanical properties, the material for the bracket does not necessarily have satisfactory adhesion to an orthodontic adhesive which is used to bond the bracket to a tooth and hence there is a fear of the bracket being separated from the surface of the tooth when it is subjected t excessive clamping force from the straightening wire.

In view of the above, according to the second technical idea of the present invention, there is provided a bracket for orthodontics which is also excellent in terms of the adhesion to the tooth surface through an orthodontic adhesive.

More specifically, according to the second technical idea of the present invention, there are provided (1) a bracket for orthodontics comprising a bracket body made of a composite resin material which is generally used as a restorative material and a thin layer of a synthetic resin material which is partly soluble or swellable in a dental adhesive, the synthetic resin thin layer being laminated on the base surface of the bracket body in such a manner that the composite resin material constituting the bracket body and the synthetic resin material constituting the thin layer are mingled with each other at the boundary therebetween, and a process for producing an orthodontic bracket comprising the steps of: supplying into a mold a composite resin paste which is generally used as a restorative material; placing a thin layer of a synthetic resin paste on the bracket base forming surface of the composite resin material, the synthetic resin paste being partly soluble or swellable in an orthodontic adhesive; and polymerizing and setting these materials.

In the present invention, the bracket body is formed from a composite resin material which is generally used as a restorative material (it is, however, necessary to somewhat modify the composition of the resin material), and a thin layer of a synthetic resin material which is partly soluble or swellable in a dental adhesive is laminated on the base surface of the bracket body. The reason for this is that excellent mechanical strength is imparted to the bracket by forming the bracket body using the above-described composite resin material and the adhesion of the bracket to an orthodontic adhesive is improved by forming the above-described synthetic resin thin layer on the base surface.

In the present invention, it is preferable from the viewpoint of mechanical strength that the synthetic resin material and the composite resin material be mingled with each other at the interfacial boundary between the base surface and the thin layer of the product, and it is therefore preferable to carry out polymerization and setting with the two materials being in contact with each other in any of the following contact states: contact of viscous liquid to viscous liquid; contact of viscous liquid to tacky resin surface; and contact of tacky resin surface to tacky resin surface.

It should be noted that the synthetic resin thin layer is only required to have a thickness of about 0.1 mm and the material for the thin layer preferably consists essentially of a PMMA (polymethyl methacrylate) having an average molecular weight of 100,000 or less or a polymethyl methacrylate copolymer.

Such a synthetic resin material readily sticks to a orthodontic adhesive and therefore contributes to achievement of satisfactorily high adhesive strength between the bracket according to the present invention and the tooth under orthodontic treatment.

The bracket material and the synthetic resin thin layer of the orthodontic bracket according to the present invention preferably have the following respective compositions.

Namely, the composite resin material that constitutes the bracket body is obtained by polymerizing and setting a mixture consisting essentially of:

(a) from 40 to 80% by weight of a multifunctional methacrylate and/or a multifunctional acrylate;

(b) from 9 to 50% by weight of a monofunctional methacrylate and/or a monofunctional acrylate;

(c) from 5 to 80% by weight of a filler; and (d) from 0.01 to 2% by weight of a polymerization initiator.

The synthetic resin thin layer laminated on the base surface of the bracket is formed by polymerizing and setting a mixture consisting essentially of:

(e) from 30 to 70% by weight of a monofunctional methacrylate;

(f) from 30 to 70% by weight of either a polymethacrylate or a copolymer thereof; and (g) from 0.01 to 1% by weight of a polymerization initiator.

According to the studies conducted by the present inventors, the bracket having the above-described composition is considerably advantageously produced by a process that employs irradiation with visible light and therefore it is preferable to use a composite resin material and synthetic resin paste of the photopolymerization type and carry out polymerization and setting by means of light irradiation.

Examples of each of the above-described compounds, that is, multifunctional methacrylate, multifunctional acrylate, monofunctional methacrylate, monofunctional acrylate, filler and polymerization initiator, may be the same as those shown in the section entitled [First Technical Idea of the Invention].

Examples of a polymethyl methacrylate or a copolymer thereof which may be used in the present invention include copolymers of methyl methacrylate and a monofunctional methacrylate, such as methyl methacrylate—ethyl methacrylate copolymer and methyl methacrylate—butyl methacrylate copolymer.

The following is a description of the reasons why the amounts of the components (a) to (d) used in the present invention are restricted within the above-described ranges.

(a) If the amount of a multifunctional methacrylate and/or a multifunctional acrylate is out of the range of from 40 to 80% by weight, for example, if it is less than 40% by weight, the fracture strength of the wings of the resulting bracket lowers, which results in an unsatisfactory product, whereas, if said amount exceeds 80% by weight, the wings of the bracket become brittle and the fracture strength thereof also lowers, which results in an unfavorable product.

(b) If the amount of a monofunctional methacrylate and/or a monofunctional acrylate used in the present invention is out of the range of from 9 to 50% by weight, for example, if it is less than 9% by weight, the bracket material becomes brittle and the fracture strength of the wings of the resulting bracket lowers, whereas, if said amount exceeds 50% by weight, the tensile strength of the bracket material lowers and the fracture strength of the wings of the bracket becomes unsatisfactory.

(c) If the amount of a filler used in the present invention is out of the range of from 5 to 80% by weight, for example, if it is less than 5% by weight, the compressive strength of the bracket material lowers, whereas, if said amount exceeds 80% by weight, the tensile strength of the material lowers and the fracture strength of the wings of the resulting bracket lowers to an unsatisfactory level.

(d) If the amount of a polymerization initiator used in the present invention is out of the range of from 0.01 to 2% by weight, for example, if it is less than 0.01% by weight, an unpolymerized substance is left in the reaction product, whereas, if said amount exceeds 2% by weight, the bracket material becomes brittle and the fracture strength of the wings of the resulting bracket lowers, which results in an unfavorable product.

In regard to the composition of the synthetic resin thin layer laminated on the bracket base, the amounts of the components (e) to (g) are restricted for the following reasons.

(e) If the amount of a monofunctional methacrylate is out of the range of from 30 to 70% by weight, for example, if it is less than 30% by weight, the viscosity of the pasty material increases so that it becomes difficult to form a synthetic resin thin layer on the bracket base, whereas, if said amount exceeds 70% by weight, the thin layer is wrinkled due to large shrinkage on polymerization.

(f) If the amount of a polymethacrylate or a copolymer thereof is out of the range of from 30 to 70% by weight, for example, if it is less than 30% by weight, the thin layer is wrinkled due to large shrinkage on polymerization.

(g) If the amount of a polymerization initiator is out of the range of from 0.01 to 1% by weight, for example, if it is less than 0.01% by weight, polymerization results in a failure, whereas, if said amount exceeds 1% by weight, foaming occurs due to excessively fast polymerization, so that the resulting thin layer is non-homogeneous.

Accordingly, it is preferable to use each component within the range specified as described above.

More preferable ranges for the components of the bracket body are as follows: (a) from 50 to 80% by weight of a multifunctional methacrylate and/or a multifunctional acrylate; (b) from 15 to 45% by weight of a monofunctional methacrylate and/or a monofunctional acrylate; (c) from 7 to 50% by weight of a filler; and (d) from 0.01 to 2% by weight of a polymerization initiator. More preferable ranges for the components of the synthetic resin thin layer laminated on the base surface of the bracket body are as follows: (e) from 40 to 60% by weight of a monofunctional methacrylate; (f) from 40 to 60% by weight of a polymethacrylate or a copolymer thereof; and (g) from 0.01 to 1% by weight of a polymerization initiator.

The bracket body of the present invention may be formed by various methods, for example, a method wherein the polymerized plastic material is machined (e.g., cutting, grinding, etc.), or a method wherein a mixture of materials such as a monomer, prepolymer, etc. is polymerized and set in a mold. It is, however, preferable to employ the latter method, i.e., the method wherein a mixture of materials is polymerized and set in a mold, because it is possible to form simultaneously the bracket body and the synthetic resin thin layer.

Examples of molds usable in the present invention include those which are made of metallic, ceramic, glass or resin materials. In the case of heat or cold polymerization, it is possible to use a mold made of a metallic, ceramic or glass material. In the case where molding process is carried out by photopolymerization, it is possible to use a mold made of a glass, light-transmitting resin or ceramic material.

The present invention will be explained more specifically below by way of Examples and Comparative Examples. However, the present invention is in no way restricted to these Examples.

EXAMPLE 2-1

Paste A (paste for constituting bracket body)

| | |
|---|---|
| Methyl methacrylate | 18 parts by weight |
| 2,2-bis-(4-methacryloxypolyethoxyphenyl) propane | 52 parts by weight |
| Aerosil R972 (manufacured by Nihon Aerosil) | 10 parts by weight |
| Glass powder | 50 parts by weight |
| N,N-dimethyl-p-toluidine | 0.3 part by weight |
| Benzoyl peroxide | 0.3 part by weight |

The above-described components were mixed together and stirred vigorously. Thereafter, the mixture was subjected to vacuum deaeration to remove completely air bubbles from the mixture, thereby preparing a paste A.

Paste B (Paste for constituting synthetic resin thin layer)

| Methyl methacrylate | 48 parts by weight |
| Polymethyl methacrylate | 52 parts by weight |
| Camphorquinone | 0.3 part by weight |
| Benzoyl peroxide | 0.3 part by weight |

The above-described components were mixed together and stirred vigorously. Thereafter, the mixture was subjected to vacuum deaeration to remove completely air bubbles from the mixture, thereby preparing a paste B.

An amount of the paste A sufficient to constitute the bracket body was first supplied into a cavity 6 defined inside the lower and side mold members 3 and 4 of a polypropylene split mold having the configuration shown in FIG. 1, and then an amount of the paste B sufficient to constitute the thin layer was injected so as to be disposed on the paste A. Thereafter, the upper mold member 5 was fitted into the cavity 6, and the mold was fixedly clamped from the upper and lower sides thereof by means of leaf springs 7 having a U-shaped cross-section. The mold was then put in a visible light irradiator—Light (manufactured by K.K Morita Tokyo Seisakusho) to irradiate the pastes A and B in the mold with light for 10 minutes.

Figure 2:
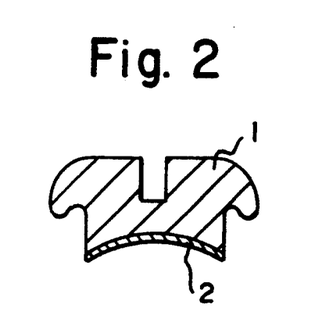
FIG. 2 is a sectional view of an orthodontic bracket according to one embodiment of the present invention.

The fracture strength of the wings of the resulting bracket (see FIG. 2) was tested in the manner described below.

As shown in FIG. 3, the bracket 1 was bonded to the surface of the enamel of a bovine tooth 12 using Superbond 11 (an adhesive manufactured by Sun Medical Co., Ltd.), the proximal portion of the bovine tooth 12 being buried in a resin 13, and this test specimen was attached to a retainer 8 made of steel. Then, the entire wing portion of the bracket 1 was held with a grab-shaped holding member 9 and the holding member 9 was pulled upward. In this way, the level of load at the time when the wing portion was fractured or deformed was measured with an Instron universal tester.

As a result of the measurement, the fracture strength of the wings of the bracket 1 was 14.7 kg and there was no separation at the interface between the bonded surfaces.

In addition, the bracket 1, which was of the same color as that of teeth, also had excellent aesthetic properties.

EXAMPLE 2-2

Paste A (paste for constituting bracket body)

| Methyl methacrylate | 18 parts by weight |
| 2,2-bis-(4-methacryloxypolyethoxyphenyl)propane | 52 parts by weight |
| Aerosil R972 (manufacured by Nihon Aerosil) | 10 parts by weight |
| Glass powder | 50 parts by weight |
| Camphorquinone | 0.1 part by weight |
| Benzoyl peroxide | 0.3 part by weight |

The above-described components were mixed together and stirred vigorously. Thereafter, the mixture was subjected to vacuum deaeration to remove completely air bubbles from the mixture, thereby preparing a paste A.

Paste B (Paste for constituting synthetic resin thin layer)

| Methyl methacrylate | 48 parts by weight |
| Polymethyl methacrylate | 52 parts by weight |
| Camphorquinone | 0.3 part by weight |
| N,N-dimethyl-p-toluidine | 0.3 part by weight |

The above-described components were mixed together and stirred vigorously. Thereafter, the mixture was subjected to vacuum deaeration to remove completely air bubbles from the mixture, thereby preparing a paste B.

As shown in FIG. 1, an amount of the paste A sufficient to constitute the bracket body was first supplied into a cavity 6 defined inside the lower and side mold members 3 and 4 of a split mold made of polypropylene, and then an amount of the paste B sufficient to constitute the thin layer was injected so as to be disposed on the paste A. Thereafter, the upper mold member 5 was fitted into the cavity 6 and the mold was fixedly clamped from the upper and lower sides thereof by means of leaf springs 7. The mold was then put in a visible light irradiator α-Light (manufactured by K.K Morita Tokyo Seisakusho) to irradiate the pastes A and B in the mold with light for 10 minutes.

The fracture strength of the wings of the resulting bracket (see FIG. 2) was tested in the manner described below.

As shown in FIG. 3, the bracket 1 was bonded to the surface of the enamel of a bovine tooth 12 using Superbond 11 (an adhesive manufactured by Sun Medical Co., Ltd.), the proximal portion of the bovine tooth 12 being buried in a resin 13, and this test specimen was attached to a retainer 8 made of steel. Then, the entire wing portion of the bracket 1 was held with a grab-shaped holding member 9 and the holding member 9 was pulled upward. In this way, the level of load at the time when the wing portion was fractured or deformed was measured with an Instron universal tester.

As a result of the measurement, the fracture strength of the wings of the bracket 1 was 13.8 kg and there was no separation at the interface between the bonded surfaces.

In addition, the bracket 1, which was of the same color as that of teeth, also had excellent aesthetic properties.

Comparative Example 2-1

The bracket in this Example is equivalent to the bracket body in Example 2-1 having no thin layer of the paste B, that is, the bracket body alone.

As shown in FIG. 1, an amount of the paste A sufficient to constitute the bracket body was supplied into a cavity 6 defined inside the lower and side mold members 3 and 4 of a split mold made of polypropylene Then, the upper mold member 5 was fitted into the cavity 6, and the mold was fixedly clamped from the upper and lower sides thereof by means of leaf springs 7. The mold was then put in a visible light irradiator α-Light (manufactured by K.K Morita Tokyo Seisakusho) to irradiate the paste A in the mold with light for 10 minutes. The resulting bracket was bonded to the surface of the enamel of a bovine tooth to measure the fracture strength of the bracket in the same manner as in Example 2-1. As a result, the base of the bracket was separated from the enamel of the bovine tooth at a load of 10.8 kg.

COMPARATIVE EXAMPLE 2-2

A bracket made of a homogeneous polycarbonate which had the same configuration as that of the cavity 6 shown in FIG. 1 was prepared by injection molding process and it was bonded to the surface of the enamel of a bovine tooth to measure the fracture strength of the wings of the bracket in the same way as in Example 2-1. As a result, the wing portion of the polycarbonate bracket was deformed at a load of 4.2 kg to such an extent that it could not be used for clinical purposes.

COMPARATIVE EXAMPLE 2-3

A commercially available ceramic bracket (manufactured by Unitec Corporation) was bonded to the surface of the enamel of a bovine tooth to measure the fracture strength of the wings of the bracket in the same way as in Example 2-1. As a result, the bracket was separated from the bovine tooth at a load of 3.5 kg.

It will be understood from the foregoing that the bracket according to the present invention has high mechanical strength and also has high strength of bond to the tooth and hence the fracture strength of the wing portions of the bracket is three times that of the prior arts shown in Comparative Examples 2-2 and 2-3.

Further, as will be clear from the results shown in Table 2-1, the bracket materials according to the present invention are also markedly superior to the polycarbonate bracket material prepared in Comparative Example 2-2 in terms of all the measured properties, i.e., hardness, tensile strength, flexural strength and compressive strength.

TABLE 2-1

|  | Brinell hardness | Tensile strength | Flexural strength | Compressive strength |
|---|---|---|---|---|
| Example 2-1 | 36 | 91 | 146 | 415 |
| Example 2-2 | 39 | 82 | 148 | 450 |
| Comp. Ex. 2-1 | 36 | 91 | 146 | 415 |
| Comp. Ex. 2-2 | 13 | 62 | 92 | 85 |

*The unit of tensile strength, flexural strength and compressive strength is MPa.

It will be further understood from the following experimental results that the orthodontic bracket according to the present invention has been satisfactorily improved in terms of adhesion to the tooth. Namely, the compression shear strength of each of the brackets prepared in the above-described Examples and Comparative Examples was measured by the following method.

Figure 4:
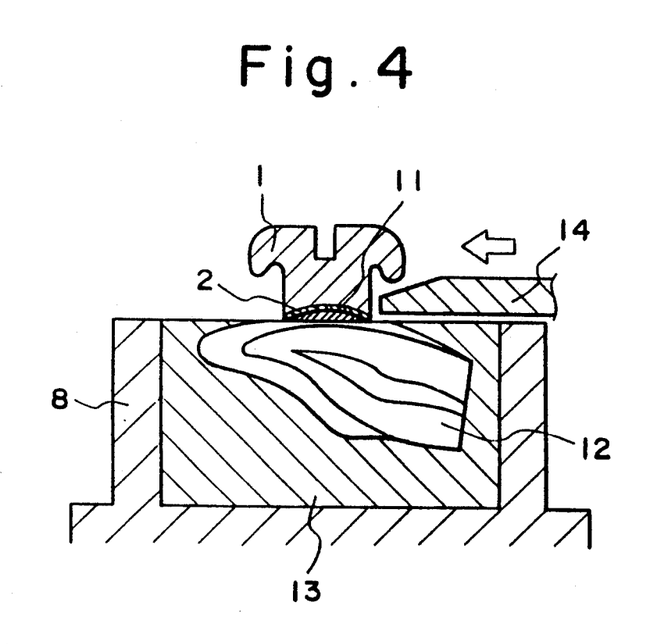
FIG. 4 illustrates a method of measuring the compression shear strength of an orthodontic bracket.

As shown in FIG. 4, Superbond 11 (a dental adhesive manufactured by Sun Medical Co., Ltd.) was applied to the base surface of the bracket 1, and the bracket base was bonded to the surface of the enamel of a bovine tooth 12 the proximal portion of which was buried in an acrylic resin 13. Thereafter, the bracket body 1 was subjected to compressive stress in the direction of the arrow by means of an Instron universal tester through a pressing member 14 to measure compression shear strength. The compression shear strength of each bracket was expressed in terms of the level of load measured at the time when the bracket base was separated from the enamel of the bovine.

TABLE 2-2

|  | Compression shear strength |
|---|---|
| Example 2-1 | 32.5 kg |
| Example 2-2 | 38.2 kg |
| Comp. Ex. 2-1 | 12.1 kg |
| Comp. Ex. 2-2 | 15.4 kg* |
| Comp. Ex. 2-3 | 3.5 kg |

*Although not separated from the tooth, the bracket was markedly deformed.

It will be understood from the experimental results that the bracket of the present invention is particularly superior in terms of compression shear strength which serves as an indication of adhesive properties Accordingly, the orthodontic bracket of the present invention has no fear of being separated from the surface of the tooth even when it is subjected to strong straightening force from the wire.

As has been described above by way of Examples, the orthodontic bracket according to the present invention has at its wing portion considerably high fracture strength, that is, fracture strength which is several times that of the conventional plastic brackets and the bracket of the present invention also has satisfactory strength of bond to the tooth. In addition, the bracket of the present invention, which is semi-transparent, i.e., milky white, has excellent aesthetic properties.

Accordingly, it is possible to produce siamese type brackets for 21 | 12 and brackets with torque angulation, which have heretofore been impossible to produce because of the inadequate mechanical strength of the plastic materials for the prior art. Further, there is no risk of the bracket being separated from the surface of the tooth even when it is subjected to excessively strong straightening force from the wire.

Since the orthodontic bracket according to the present invention is excellent in terms of various mechanical properties, i.e., tensile strength, flexural strength, compressive strength, etc., it is also possible to reduce the required size of the bracket. Therefore, a patient who has this bracket attached to his tooth feels less uncomfortable with the foreign matter in his mouth.

Since the surface hardness of the bracket according to the present invention is markedly higher than that of the prior art, there is no fear of the surface of the bracket being contaminated due to scratches which would otherwise be made with a toothbrush or the like.

Thus, the bracket according to the present invention not only has satisfactory initial strength but also exhibits high mechanical strength over a long period of time and therefore is free from the fear of fracture or surface contamination even if it is used for a long time.

Third Technical Idea of the Invention

According to the third technical idea of the present invention, there is provided a bracket for orthodontics which has superior aesthetic properties and enhanced mechanical strength and further has improved adhesion to the tooth.

More specifically, the followings are provided according to the third technical idea of the present invention:

(1) A bracket for orthodontics comprising a bracket body formed from a composite resin material A obtained by polymerizing and setting a mixture consisting essentially of
  (a) from 40 to 80% by weight of a multifunctional methacrylate and/or a multifunctional acrylate, (b) from 9 to 50% by weight of a monofunctional methacrylate and/or a monofunctional acrylate,
(c) from 5 to 80% by weight of a filler, and
(d) from 0.01 to 2% by weight of a polymerization initiator, and a thin layer of a composite resin material B obtained by polymerizing and setting a mixture consisting essentially of (e) from 5 to 24% by weight of a multifunctional methacrylate,
(f) from 0 to 24% by weight of a monofunctional methacrylate,
(g) from 50 to 90% by weight of a silica filler, and
(h) from 0.01 to 1% by weight of a polymerization initiator, the thin layer being laminated on the base surface of the bracket body in such a manner that the composite resin material A constituting the bracket body and the composite resin material B constituting the thin layer are mingled with each other at the boundary therebetween.

(2) A process for producing an orthodontic bracket comprising the steps of: supplying into a mold a composite resin paste A consisting essentially of (a) from 40 to 80% by weight of a multifunctional methacrylate and/or a multifunctional acrylate,
(b) from 9 to 50% by weight of a monofunctional methacrylate and/or a monofunctional acrylate,
(c) from 5 to 80% by weight of a filler, and
(d) from 0.01 to 2% by weight of a polymerization initiator;

placing on the bracket base forming surface of the composite resin paste A a composite resin paste B consisting essentially of (e) from 5 to 24% by weight of a multifunctional methacrylate,
(f) from 0 to 24% by weight of a monofunctional methacrylate,
(g) from 50 to 90% by weight of a silica filler, and
(h) from 0.01 to 1% by weight of a polymerization initiator;

and polymerizing and setting these materials.

In the present invention, the bracket body is formed from a composite resin material which is essentially used as a restorative material and a thin layer of a composite resin material B which is adhesive to a dental adhesive is laminated on the base surface of the bracket body in the same way as in [Second Technical Idea of the Invention]. The reason for this is that excellent mechanical strength and superior aesthetic properties are imparted to the bracket by forming the bracket body using the above-described composite resin material and the adhesion of the bracket to an orthodontic adhesive is improved by forming the above-described composite resin B thin film on the base surface.

In the present invention, it is preferable from the viewpoint of mechanical strength that the composite resin material B and the composite resin material A be mingled with each other at the interfacial boundary between the base surface and the thin layer of the product, and it is therefore preferable to carry out polymerization and setting with the two materials being in contact with each other in any of the following contact states: contact of viscous liquid to viscous liquid; contact of viscous liquid to tacky resin surface; and contact of tacky resin surface to tacky resin surface.

It should be noted that the composite resin B thin layer is only required to have a thickness of about 0.1 mm The above-described composite resin material B does not easily stick to a dental adhesive in this state. However, the composite resin material B which has been treated with a silane coupling agent firmly bonds to a dental adhesive and therefore contributes to satisfactorily enhancing the bond strength of the bracket of the present invention with respect to the tooth under orthodontic treatment.

The bracket material and the composite resin B thin layer of the orthodontic bracket according to the present invention preferably have the following respective compositions.

Namely, the composite resin material A that constitutes the bracket body is formed by polymerizing and setting a mixture consisting essentially of:

(a) from 40 to 80% by weight of a multifunctional methacrylate and/or a multifunctional acrylate;
(b) from 9 to 50% by weight of a monofunctional methacrylate and/or a monofunctional acrylate;
(c) from 5 to 80% by weight of a filler; and
(d) from 0.01 to 2% by weight of a polymerization initiator.

The composite resin material B thin layer that is laminated on the base surface of the bracket body is formed by polymerizing and setting a mixture consisting essentially of:

(e) from 5 to 24% by weight of a multifunctional methacrylate;
(f) from 0 to 24% by weight of a monofunctional methacrylate;
(g) from 50 to 90% by weight of a silica filler; and
(h) from 0.01 to 1% by weight of a polymerization initiator, the thin layer being laminated on the base surface of the bracket body in such a manner that the composite resin material A constituting the bracket body and the composite resin material B constituting the thin layer are mingled with each other at the boundary therebetween.

According to the studies conducted by the present inventors, the bracket having the above-described composition is considerably advantageously produced by a process that employs irradiation with visible light and therefore it is preferable to use a composite resin material A and composite resin paste B of the photopolymerization type and carry out polymerization and setting by means of light irradiation.

Examples of each of the above-described compounds, that is, multifunctional methacrylate, multifunctional acrylate, monofunctional methacrylate, monofunctional acrylate, filler and polymerization initiator, may be the same as those shown in the section entitled [First Technical Idea of the Invention].

The following is a description of the reasons why the amounts of the components (a) to (d) used in the present invention are restricted within the above-described ranges.

(a) If the amount of a multifunctional methacrylate and/or a multifunctional acrylate is out of the range of from 40 to 80% by weight, for example, if it is less than 40% by weight, the fracture strength of the wings of the resulting bracket lowers, which results in an unsatisfactory product, whereas, if said amount exceeds 80% by weight, the wings of the bracket become brittle and the fracture strength thereof lowers and further the luster of the bracket surface is lost, which results in an unfavorable product.

(b) If the amount of a monofunctional methacrylate and/or a monofunctional acrylate used in the present invention is out of the range of from 9 to 50% by weight, for example, if it is less than 9% by weight, the bracket material becomes brittle and the fracture strength of the wings of the resulting bracker lowers, whereas, if said amount exceeds 50% by weight, the tensile strength of the bracket material lowers and the fracture strength of the wings of the bracket becomes unsatisfactory.

(c) If the amount of a filler used in the present invention is out of the range of from 5 to 80% by weight, for example, if it is less than 5% by weight, the compressive strength of the bracket material lowers, whereas, if said amount exceeds 80% by weight, the tensile strength of the material lowers and the fracture strength of the wings of the resulting bracket lowers to an unsatisfactory level.

(d) If the amount of a polymerization initiator used in the present invention is out of the range of from 0.01 to 2% by weight, for example, if it is less than 0.01% by weight, an unpolymerized substance is left in the reaction product, whereas, if said amount exceeds 2% by weight, the bracket material becomes brittle and the fracture strength of the wings of the resulting bracket lowers, which results in an unfavorable product.

In regard to the composition of the composite resin B thin layer laminated on the bracket base, the amounts of the components (e) to (h) are restricted for the following reasons.

(e) If the amount of a multifunctional methacrylate is out of the range of from 5 to 24% by weight, for example, if it is less than 5% by weight, the strength of the composite resin B thin layer is excessively low, whereas, if said amount exceeds 24% by weight, the adhesion of the thin layer lowers.

(f) If the amount of a monofunctional methacrylate is out of the range of from 0 to 24% by weight, for example, if it exceeds 24% by weight, the thin layer is wrinkled due to large shrinkage on polymerization and the bond strength also lowers.

(g) If the amount of a silica filler is out of the range of from 50 to 90% by weight, for example, if it is less than 50% by weight, the adhesion of the thin layer lowers, whereas, if said amount exceeds 90% by weight, it becomes impossible to produce a pasty material.

(h) If the amount of a polymerization initiator is out of the range of from 0.01 to 1% by weight, for example, if it is less than 0.01% by weight, polymerization results in a failure, whereas, if said amount exceeds 1% by weight, foaming occurs due to excessively fast polymerization, so that the resulting thin layer is non-homogeneous.

Accordingly, it is preferable to use each component within the range specified as described above.

More preferable ranges for the components of the bracket body are as follows: (a) from 50 to 80% by weight of a multifunctional methacrylate and/or a multifunctional acrylate; (b) from 15 to 45% by weight of a monofunctional methacrylate and/or a monofunctional acrylate; (c) from 7 to 50% by weight of a filler; and (d) from 0.01 to 2% by weight of a polymerization initiator. More preferable ranges for the components of the composite resin thin layer laminated on the base surface of the bracket body are as follows: (e) from 5 to 20% by weight of a multifunctional methacrylate; (f) from 5 to 20% by weight of a monofunctional methacrylate; (g) from 60 to 85% by weight of a silica filler; and (h) from 0.01 to 1% by weight of a polymerization initiator.

The bracket body of the present invention ma be formed by various methods, for example, a method wherein the polymerized plastic material is machined (e.g., cutting, grinding, etc.), or a method wherein a mixture of materials such as a monomer, prepolymer, etc. is polymerized and set in a mold. It is, however, preferable to employ the latter method, i e., the method wherein a mixture of materials is polymerized and set in a mold, because it is possible to form simultaneously the bracket body and the composite resin B thin layer.

Examples of molds usable in the present invention include those which are made of metallic, ceramic, glass or resin materials. In the case of heat or cold polymerization, it is possible to use a mold made of a metallic, ceramic or glass material. In the case where molding process is carried out by photopolymerization, it is possible to use a mold made of a glass, light-transmitting resin or ceramic material.

The present invention will be explained more specifically below by way of Examples and Comparative Examples. However, the present invention is in no way restricted to these Examples.

EXAMPLE 3-1

Paste A (paste for constituting bracket body)

| | |
|---|---|
| Methyl methacrylate | 18 parts by weight |
| 2,2-bis-(4-methacryloxypolyethoxyphenyl) propane | 52 parts by weight |
| Aerosil R972 (manufacured by Nihon Aerosil) | 10 parts by weight |
| Glass powder | 20 parts by weight |
| Benzoyl peroxide | 0.3 part by weight |
| N,N-dimethyl-p-toluidine | 0.3 part by weight |

The above-described components were mixed together and stirred vigorously. Thereafter, the mixture was subjected to vacuum deaeration to remove completely air bubbles from the mixture, thereby preparing a paste A.

Paste B (Paste for constituting composite resin thin layer)

| | |
|---|---|
| Methyl methacrylate | 2 parts by weight |
| 2,2-bis(p-2'-hydroxy-3-methacryloxypropoxyphenyl) propane | 13 parts by weight |
| Glass powder | 85 parts by weight |
| Camphorquinon | 0.3 part by weight |
| Benzoyl peroxide | 0.3 part by weight |

The above-described components were mixed together and stirred vigorously. Thereafter, the mixture was subjected to vacuum deaeration to remove completely air bubbles from the mixture, thereby preparing a paste B.

An amount of the paste A sufficient to constitute the bracket body was first supplied into a cavity 6 defined inside the lower and side mold members 3 and 4 of a polypropylene split mold having the configuration shown in FIG. 1, and then an amount of the paste B sufficient to constitute the thin layer was injected so as to be disposed on the paste A. Thereafter, the upper mold member 5 was fitted into the cavity 6, and the mold was fixedly clamped from the upper and lower sides thereof by means of leaf springs 7. The mold was then put in a visible light irradiator α-Light (manufactured by K.K Morita Tokyo Seisakusho) to irradiate the pastes A and B in the mold with light for 10 minutes.

The fracture strength of the wings of the resulting bracket (see FIG. 2) was tested in the manner described below.

After Porcelain liner M (a dental silane coupling agent manufactured by Sun Medical Co., Ltd.) had been applied to the base surface of the bracket 1, as shown in FIG. 3, the bracket 1 was bonded to the surface of the enamel of a bovine tooth 12 using Superbond 11 (an adhesive manufactured by Sun Medical Co., Ltd.), the proximal portion of the bovine tooth 12 being buried in a resin 13, and this test specimen was attached to a retainer 8 made of steel. Then, the entire wing portion of the bracket 1 was held with a grab-shaped holding member 9 and the holding member 9 was pulled upward. In this way, the level of load at the time when the wing portion was fractured or deformed was measured with an Instron universal tester.

As a result of the measurement, the fracture strength of the wings of the bracket 1 was 14.2 kg and there was no separation at the interface between the bonded surfaces.

In addition, the bracket 1, which was of the same color as that of teeth, also had excellent aesthetic properties.

EXAMPLE 3-2

Paste A (paste for constituting bracket body)

| | |
|---|---|
| Methyl methacrylate | 18 parts by weight |
| 2,2-bis-(4-methacryloxypolyethoxyphenyl) propane | 52 parts by weight |
| Aerosil R972 (manufacured by Nihon Aerosil | 20 parts by weight |
| Trimethylolpropane trimethacrylate | 10 parts by weight |
| Camphorquinone | 0.1 part by weight |
| Benzoyl peroxide | 0.3 part by weight |

The above-described components were mixed together and stirred vigorously. Thereafter, the mixture was subjected to vacuum deaeration to remove completely air bubbles from the mixture, thereby preparing a paste A.

Paste B (Paste for constituting synthetic resin thin layer)

| | |
|---|---|
| Di-(methacryloxyethyl) trimethylhexane diurethane | 35 parts by weight |
| Triethylene glycol dimethacrylate | 10 parts by weight |
| Quarts powder | 55 parts by weight |
| Camphorquinone | 0.3 part by weight |
| N,N-dimethyl-p-toluidine | 0.3 part by weight |

The above-described components were mixed together and stirred vigorously Thereafter, the mixture was subjected to vacuum deaeration to remove completely air bubbles from the mixture, thereby preparing a paste B.

As shown in FIG. 1, an amount of the paste A sufficient to constitute the bracket body was first supplied into a cavity 6 defined inside the lower and side mold members 3 and 4 of a split mold made of polypropylene, and then an amount of the paste B sufficient to constitute the thin layer was injected so as to be disposed on the paste A. Thereafter, the upper mold member 5 was fitted into the cavity 6, and the mold was fixedly clamped from the upper and lower sides thereof by means of leaf springs 7. The mold was then put in a visible light irradiator α-Light (manufactured by K.K Morita Tokyo Seisakusho) to irradiate the pastes A and B in the mold with light for 10 minutes.

The fracture strength of the wings of the resulting bracket (see FIG. 2) was tested in the manner described below.

After Porcelain liner M (a dental silnane coupling agent manufactured by Sun Medical Co., Ltd.) had been applied to the base surface of the bracket 1, as shown in FIG. 3, the bracket 1 was bonded to the surface of the enamel of a bovine tooth 12 using Superbond 11 (an adhesive manufactured by Sun Medical Co., Ltd.), the proximal portion of the bovine tooth 12 being buried in a resin 13, and this test specimen was attached to a retainer 8 made of steel. Then, the entire wing portion of the bracket 1 was held with a grab-shaped holding member 9 and the holding member 9 was pulled upward. In this way, the level of load at the time when the wing portion was fractured or deformed was measured with an Instron universal tester.

As a result of the measurement, the fracture strength of the wings of the bracket 1 was 14.2 kg and there was no separation at the interface between the bonded surfaces.

In addition, the bracket 1, which was of the same color as that of teeth, also had excellent aesthetic properties.

COMPARATIVE EXAMPLE 3-1

The bracket in this Example is equivalent to the bracket body in Example 3-1 having no thin layer of the paste B, that is, the bracket body alone.

As shown in FIG. 1, an amount of the paste A sufficient to constitute the bracket body was supplied into a cavity 6 defined inside the lower and side mold members 3 and 4 of a split mold made of polypropylene. Then, the upper mold member 5 was fitted into the cavity 6, and the mold was fixedly clamped from the upper and lower sides thereof by means of leaf springs 7. The mold was then put in a visible light irradiator α-Light (manufactured by K.K Morita Tokyo Seisakusho) to irradiate the paste A in the mold with light for 10 minutes. The resulting bracket was bonded to the surface of the enamel of a bovine tooth to measure the fracture strength of the bracket in the same manner as in Example 3-1. As a result, the fracture strength was 13.4 kg.

COMPARATIVE EXAMPLE 3-2

A bracket made of a homogeneous polycarbonate which had the same configuration as that of the cavity 6 shown in FIG. 1 was prepared by injection molding process and it was bonded to the surface of the enamel of a bovine tooth to measure the fracture strength of the wings of the bracket in the same way as in Example 3-1. As a result, the wing portion of the polycarbonate bracket was deformed at a load or 4.2 kg to such an extent that it could not be used for clinical purposes.

COMPARATIVE EXAMPLE 3-3

A commercially available ceramic bracket (manufactured by Unitec Corporation) was bonded to the surface of the enamel of a bovine tooth to measure the fracture strength of the wings of the bracket in the same way as in Example 3-1. As a result, the bracket was separated from the bovine tooth at a load of 3.5 kg.

It will be understood from the foregoing that the bracket according to the present invention has high mechanical strength and also has high strength of bond to the tooth and hence the fracture strength of the wing portions of the bracket is three times that of the prior arts shown in Comparative Examples 3-2 and 3-3.

Further, as will be clear from the results shown in Table 3-1, the bracket materials according to the present invention are also markedly superior to the polycarbonate bracket material prepared in Comparative Example 3-2 in terms of all the measured properties, i.e., hardness, tensile strength, flexural strength and compressive strength.

TABLE 3-1

|  | Brinell hardness | Tensile strength | Flexural strength | Compressive strength |
| --- | --- | --- | --- | --- |
| Example 3-1 | 34 | 98 | 138 | 385 |
| Example 3-2 | 30 | 94 | 132 | 368 |
| Comp. Ex. 3-1 | 36 | 91 | 146 | 368 |
| Comp. Ex. 3-2 | 13 | 62 | 92 | 85 |

*The unit of tensile strength, flexural strength and compressive strength is MPa.

It will be further understood from the following experimental results that the orthodontic bracket according to the present invention has been satisfactorily improved in terms of adhesion to the tooth. Namely, the compression shear strength of each of the brackets prepared in the above-described Examples and Comparative Examples was measured by the following method.

As shown in FIG. 4, after Porcelain liner M (a silica coupling agent manufactured by Sun Medical Co., Ltd.) had been applied to the base surface of the bracket 1, Superbond 11 (a dental adhesive manufactured by Sun Medical Co., Ltd.) was applied to the base surface of the bracket 1, and the bracket base was then bonded to the surface of the enamel of a bovine tooth 12 the proximal portion of which was buried in an acrylic resin 13. Thereafter, the bracket body 1 was subjected to compressive stress in the direction of the arrow by means of an Instron universal tester through a pressing member 14 to measure compression shear strength. The compression shear strength of each bracket was expressed in terms of the level of load measured at the time when the bracket base was separated from the enamel of the bovine.

TABLE 3-2

|  | Compression shear strength |
| --- | --- |
| Example 3-1 | 40.5 kg |
| Example 3-2 | 31.1 kg |
| Comp. Ex. 3-1 | 12.1 kg |
| Comp. Ex. 3-2 | 15.4 kg* |
| Comp. Ex. 3-3 | 3.5 kg |

* Although not separated from the tooth, the bracket was markedly deformed.

It will be understood from the experimental results that the bracket of the present invention is particularly superior in terms of compression shear strength which serves as an indication of adhesive properties.

Accordingly, the orthodontic bracket of the present invention has no fear of being separated from the surface of the tooth even when it is subjected to strong straightening force from the wire.

As has been described above by way of Examples, the orthodontic bracket according to the present invention has at its wing portion considerably high fracture strength, that is, fracture strength which is several times that of the conventional plastic brackets and the bracket of the present invention also has satisfactory strength of bond to the tooth. In addition, the bracket of the present invention, which is semi-transparent, i.e., milky white, has excellent aesthetic properties.

Accordingly, it is possible to produce siamese type brackets for 21 | 12 and brackets with torque angulation, which have heretofore been impossible to produce because of the inadequate mechanical strength of the plastic materials for the prior art. Further, there is no risk of the bracket being separated from the surface of the tooth even when it is subjected to excessively strong straightening force from the wire.

Since the orthodontic bracket according to the present invention is excellent in terms of various mechanical properties, i.e., tensile strength, flexural strength, compressive strength, etc., it is also possible to reduce the required size of the bracket. Therefore, a patient who has this bracket attached to his tooth feels less uncomfortable with the foreign matter in his mouth.

Since the surface hardness of the bracket according to the present invention is markedly higher than that of the prior art, there is no fear of the surface of the bracket being contaminated due to scratches which would otherwise be made with a toothbrush or the like.

Thus, the bracket according to the present invention not only has satisfactory initial strength but also exhibits high mechanical strength over a long period of time and therefore is free from the fear of fracture or surface contamination even if it is used for a long time.

What we claim is:

1. A bracket for orthodontics comprising:
    a bracket body made of a composite resin material; and
    a thin layer of a synthetic resin material which consists essentially of a polymethyl methacrylate having an average molecular weight of 100,000 or less or a polymethyl methacrylate copolymer, the synthetic resin thin layer being laminated on the base surface of said bracket body in such a manner that the composite resin material constituting the bracket body and the synthetic resin material constituting said thin layer are mingled with each other at the boundary therebetween.

2. A bracket for orthodontics according to claim 1, wherein the composite resin material that constitutes said bracket body is formed by polymerizing and setting a mixture consisting essentially of
    (a) from 40 to 80% by weight of a multifunctional methacrylate and/or a multifunctional acrylate,
    (b) from 9 to 50% by weight of a monofunctional methacrylate and/or a monofunctional acrylate,
    (c) from 5 to 80% by weight of a filler, and
    (d) from 0.01 to 2% by weight of a polymerization initiator,
    and the synthetic resin thin layer laminated on the base surface of said bracket body is formed by polymerizing and setting a mixture consisting essentially of
    (e) from 30 to 70% by weight of a monofunctional methacrylate,
    (f) from 30 to 70% by weight of either a polymethacrylate or a copolymer thereof, and
    (g) from 0.01 to 1% by weight of a polymerization initiator;

3. A bracket for orthodontics comprising:

a bracket body made of a composite resin material A obtained by polymerizing and setting a mixture consisting essentially of
(a) from 40 to 80% by weight of a multifunctional methacrylate and/or a multifunctional acrylate,
(b) from 9 to 50% by weight of a monofunctional methacrylate and/or a monofunctional acrylate,
(c) from 5 to 80% by weight of a filler, and
(d) from 0.01 to 2% by weight of a polymerization initiator;
and a thin layer of a composite resin material B obtained by polymerizing and setting a mixture consisting essentially of (e) from 5 to 24% by weight of a multifunctional methacrylate,
(f) from 0 to 24% by weight of a monofunctional methacrylate,
(g) from 50 to 90% by weight of a silica filler, and
(h) from 0.01 to 1% by weight of a polymerization initiator,
said thin layer of the composite resin material B being laminated on the base surface of said bracket body in such a manner that the composite resin material A constituting said bracket body and the composite resin material B constituting said thin layer are mingled with each other at the boundary therebeween.

* * * * *

UNITED STATES PATENT AND TRADEMARK OFFICE
CERTIFICATE OF CORRECTION

PATENT NO. : 5,147,202
DATED     : September 15, 1992
INVENTOR(S) : Eiichi MASUHARA et al.

It is certified that error appears in the above-identified patent and that said Letters Patent is hereby corrected as shown below:

On the cover page, Item [54], the title "BRACKET FOR ORTHODONTICS" should read   --BRACKET FOR ORTHODONTICS AND PROCESS FOR PRODUCING THE SAME--.

On the cover page, Item [57], line 11, "1000,000" should read --100,000--.

On the cover page, Item [75], line 3, the inventor's city "Yomo" should read --Yono--.

Signed and Sealed this

Second Day of November, 1993

Attest:

BRUCE LEHMAN

*Attesting Officer*     *Commissioner of Patents and Trademarks*